United States Patent [19]

Machoczek

[11] Patent Number: 6,066,335
[45] Date of Patent: May 23, 2000

[54] METHOD OF PRODUCING EFFERVESCENT TABLETS AND EFFERVESCENT TABLET

[75] Inventor: Horst Machoczek, Allensteinstr. 28, D-37130 Gleichen, Germany

[73] Assignee: Horst Machoczek, Gleichen, Germany

[21] Appl. No.: 08/677,591

[22] Filed: Jul. 9, 1996

[51] Int. Cl.$^7$ ............................... A61K 9/46; A61K 47/10
[52] U.S. Cl. ......................... 424/466; 264/109; 514/960; 514/961
[58] Field of Search ........................... 424/466; 264/109; 518/960, 961

[56] References Cited

U.S. PATENT DOCUMENTS

| | | | |
|---|---|---|---|
| 3,024,165 | 3/1962 | Murphy | 424/466 |
| 4,725,427 | 2/1988 | Ashmead et al. | 424/44 |

FOREIGN PATENT DOCUMENTS

| | | |
|---|---|---|
| 0070127A3 | 1/1983 | European Pat. Off. |
| 0085376A2 | 1/1983 | European Pat. Off. |
| 0219337A2 | 10/1986 | European Pat. Off. |
| 0219337A3 | 4/1987 | European Pat. Off. |
| 0395329A3 | 10/1990 | European Pat. Off. |
| 2409789 | 6/1979 | France. |
| Nr 308 284 | 5/1969 | Germany. |
| E 55 055 | 5/1986 | Germany. |
| 63-264518 | 1/1988 | Japan. |

OTHER PUBLICATIONS

Einführung in die Verfahrenstechnik Der Arzneiformung, von Dr. Fritz Gstirner, Stuttgart, 1972.

*Primary Examiner*—Frederick Krass
*Attorney, Agent, or Firm*—Thomas, Kayden, Horstemeyer & Risley

[57] ABSTRACT

A method of producing mechanically stable effervescent tablets with a high dissolving velocity and an according effervescent tablet are described. The effervescent tablets consist of at least one active substance or of a combination of active substances, of at least one binder, of possibly carriers as sweeteners, flavors, colorings, scents, softeners, bleaches, and of sherbets. In producing, propylglycol or glycerin is used as a binder for the effervescent tablets, and the active substances or the combination of active substances and possibly carriers are mixed with the binder. Afterwards, the sherbets are added to this mixture in an air-conditioned room. Then, the mixture including the sherbets is formed into tablets.

15 Claims, 1 Drawing Sheet

METHOD OF PRODUCING EFFERVESCENT TABLETS AND EFFERVESCENT TABLET

FIELD OF THE INVENTION

The invention relates to a method of producing effervescent tablets which consist of at least one active substance or a combination of active substances, of at least one binder, possibly of carriers as sweeteners, flavours, colourings, scents, softeners and bleaches, and of sherbets, wherein the active substance or the combination of active substances and possibly the carriers are mixed with the binder, wherein the sherbets are added to this mixture in an air-conditioned room, and wherein the mixture including the sherbets is formed into tablets. The invention also relates to an effervescent tablet which consists of at least one active substance or a combination of active substances, of at least one binder, possibly of carriers as sweeteners, flavours, colourings, scents, softeners and bleaches, and of sherbets.

PRIOR ART

To produce effervescent tablets it is known to form granules as a pre-step for the effervescent tablet. Such granules are, however, connected with difficulties since the sherbets of a effervescent tablet are extremely sensitive to humidity and for example adding water to the sherbets always causes a setting free of the carbon dioxide bound in the sherbets.

Besides the methods based on granulating the used substances also methods to produce effervescent tablets are known by which the substances are directly formed into tablets. Such a method is for example described in the European Patent Application 0 219 337. According to this method powdery dextrose or sucrose is used as a binder for the effervescent tablets. In comparative examples of the European Patent Application this binder is compared with different sugar substitutes as a binder. When using dextrose and/or sucrose as a binder the amount of binder is 10 to 40% per weight of the whole effervescent tablet.

OBJECT OF THE INVENTION

It is the object of the invention to provide a simple method of producing stable effervescent tablets having a short dissolving time wherein any active substance or any combination of substances can be used and wherein only a small amount of binder compared to the whole weight of the effervescent tablet is needed. Further, a effervescent tablet is to be provided that can be easily produced and is mechanically stable and dissolves quickly.

SUMMARY OF THE INVENTION

According to the invention there is provided a method of producing effervescent tablets which consist of at least one active substance or a combination of active substances, of at least one binder, possibly of carriers as sweeteners, flavours, colourings, scents, softeners and bleaches, and of sherbets, wherein propylglycol or glycerin is used as a binder, wherein the active substance or the combination of active substances and possibly the carriers are mixed with the binder, wherein the sherbets are added to this mixture in an air-conditioned room and wherein the mixture including the sherbets is formed into tablets.

Further, according to the invention there is provided a effervescent tablet consisting of at least one active substance or one combination of active substances, of at least one binder, possibly of carriers as sweeteners, flavours, colourings, scents, softeners and bleaches, and of sherbets, which comprise propylglycol or glycerin as a binder.

Propylglycol or glycerin as a binder are only needed in small amounts to achieve the wanted mechanical characteristics of the effervescent tablets and to keep the wanted dissolving attitude. Handling the binder propylglycol or glycerin is also very simple. It can be mixed with the active substance or with the combination of active substances and possibly with the carrier without destroying their tipping ability and thus their simple ability to be mixed with the sherbets. At the same time there is no danger that the binder could cause a loss of carbon dioxide of the sherbets.

The active substances to be used in the method and for the effervescent tablet according to the invention are not limited at all. They include, for example, calcium, magnesium, potassium, iron-II-gluconate, vitamin E, vitamin C, paracetamol, cimetidine, piracetam, acetylsalicyl acid, ambroxol, indomethacin and acetylcysteine or any other active substance.

The combination of substances to be used includes for example multi vitamins, multi vitamins with minerals, beta carotin with vitamin E and/or vitamin C, vitamin C with minerals, anionic and/or not-ionic tensides or other washing active substances. Also all combinations of active substances which can be orally taken in solving form can be used.

The possibly used carriers can be flavourings such as sweeteners, sugar substitutes, flavours or additional or alternate further carriers as colourings or scents. These carriers are well known by those of ordinary skill in the art. The definite choice depends on the wanted result, especially with respect to the taste of the dissolved effervescent tablets, and lies within the knowledge of those skilled in the art.

Those skilled in the art also know possible compositions of sherbets for the effervescent tablets. These sherbets consist of a base component and an acid component wherein especially the acid component also can be used as an active substance. One known example thereof is ascorbic acid (vitamin C). Usually, as base component sodium carbonate, sodium hydrogen carbonate, potassium carbonate, potassium hydrogen carbonate and calcium carbonate are used. As an acid component besides ascorbic acid mono sodium citrate, wine acid and/or citric acid can be considered.

Advantageously, the method according to the invention includes intensely mixing the active substance or the combination of active substances and possibly carriers with the binder before adding the sherbets, and directly forming a mixture including the sherbets into tablets. Advantageously, in case of both the method and the effervescent tablet according to the invention the amount of binder is in the range of 0.004 to 2.5% per weight of the whole effervescent tablets, especially in the range of 0.004 to 1.5% per weight of the whole effervescent tablets, and more especially in the range of 0.01 to 1.0% per weight of the whole effervescent tablets. Further, the amount of sherbets advantageously is in the range of 58 to 93% per weight of the whole effervescent tablets, and especially in the range of 70 to 90% per weight of the whole effervescent tablets.

An important advantage of the new method of producing the effervescent tablets is the small apparatus and the short time needed by equally great freedom concerning the used active substances or combination of substances. Thus, the method can be used to produce pharmaceutical effervescent tablets as well as diet effervescent tablets and tablets for washing, bathing and decalcifying.

BRIEF DESCRIPTION OF THE DRAWINGS

The invention will further be explained by means of the following examples and with reference to the following drawings in which.

DETAILED DESCRIPTION OF THE PREFERRED EMBODIMENTS

Figures 1, 2:
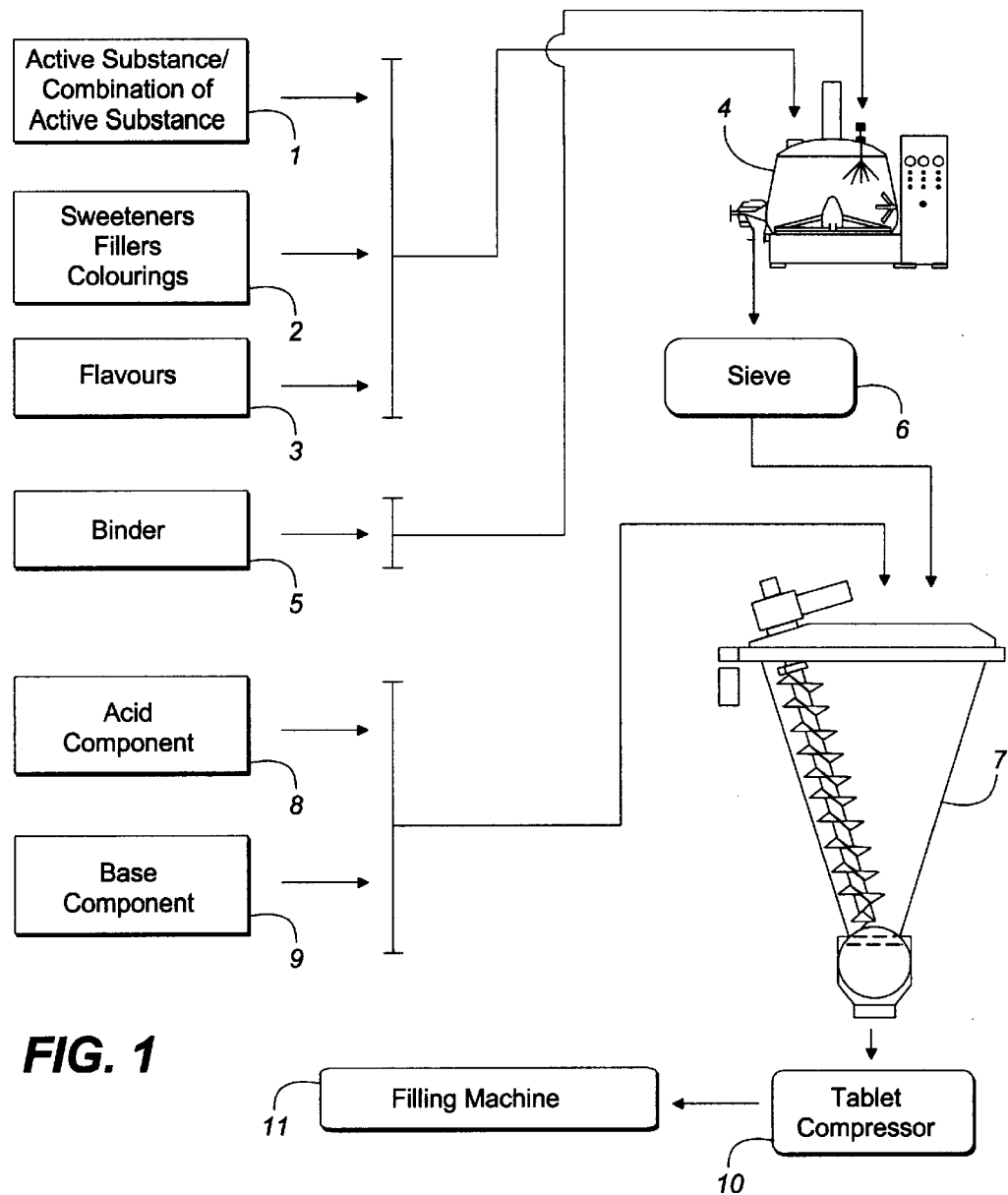
FIG. 1 is a flow-chart of a process according to the method of the invention and FIG. 2 shows two effervescent tablets according to the invention, one in top view and the other one in side view.

In all examples, the procedure follows the process shown in FIG. 1. An active substance or a combination of active substances 1 is mixed with sweeteners, fillers and colourings 2 as well as with flavours 3 in a high shear mixer 4. Afterwards, the binder 5 is sprayed upon the mixture and the mixture is once again intensely mixed. Then the content of the high shear mixer 4 is transferred over a sieve 6 with a mesh of 1 mm into a blender 7. In the blender 7 the sherbets which consist of an acid component 8 and a base component 9 are added. After mixing in the blender 7 the tablet blend is transferred to a tablet compressor 10. The resulting effervescent tablets then reach the filling machine 11.

In the following, the equipment is listed which is actually used in the examples:
Weighing
Floor balance
  Type: ID 5 MULTIRANGE Manufacturer: Mettler, GieBen, Germany
Desk balance
  Type: ID 5 MULTIRANGE Manufacturer: Mettler, GieBen, Germany
Manufacture of the tablet blend High shear mixer/granulator

| Type: DIOSNA P 400 | Manufacturer: | Dierks & Söhne, Osnabrück, Germany |

Oscillating sieve

| Type: MGIF 634 | Manufacturer: | Frewitt, Fribourg, Switzerland |

Blender

| Type: PM 1000 | Manufacturer: | L.B. Bohle, Ennigerloh, Germany, or |
| Type: ROBA 500 | Manufacturer: | Peterhans, Dottikon, Switzerland |

Tabletting
Tablet compressor with external lubrication device
  Type: P 1000 Manufacturer: Fette, Schwarzenbek, Germany Testing and In process control Hardness tester

| Type: 6 D | Manufacturer: | Schleuniger, Solothurn, Switzerland |

Desk balance

| Type: 1408 0042 | Manufacturer: | Sartorius, Göttingen, Germany |

EXAMPLE 1.1

Acetylsalicyl Acid 500 Mg Effervescent Tablet

| 100.000 kg | acetylsalicyl acid |
| 10.000 kg | primary sodium phosphate |
| 4.000 kg | Tylose C 300 P | are mixed for 3 min in the high shear mixer 4.
0.100 kg propylglycol are added and the mixture is once again briefly mixed.

The acetylsalicyl acid-concentrate is mixed in an air-conditioned room (relative humidity <25%) in the blender 7 with

| 186.000 kg | citric acid |
| 240.000 kg | sodium hydrogen carbonate | for about 10 to 15 min.

The obtained 539.900 kg tablet blend is pressed by a tablet compressor under external lubrication with less than 0.100 kg magnesium stearate into 200.000 round tablets with a diameter of 22 mm and a tablet weight of 2.7 g.

The tablet hardness is 45 to 55 N.

EXAMPLE 1.2

Acetylsalicyl Acid+Vitamin C Effervescent Tablet

| 75.000 kg | acetylsalicyl acid |
| 18.750 kg | ascorbic acid |
| 3.000 kg | primary sodium phosphate |
| 1.350 kg | sodium saccharinate |
| 4.500 kg | fruit flavour | are mixed for 3 min in the high shear mixer 4.
0.075 kg propylglycol are added and the mixture is once again briefly mixed.

The acetylsalicyl acid-vitamin C-sweetener-flavour-concentrate is mixed in an air-conditioned room (relative humidity <25%) in the blender 7 with

| 182.400 kg | citric acid |
| 254.850 kg | sodium bicarbonate | for about 10 to 15 min.

The obtained 539.925 kg tablet blend is pressed by a tablet compressor under external lubrication with less than 0.075 kg magnesium stearate into 150.000 round tablets with a diameter of 25 mm and a tablet weight of 3.6 g.

The tablet hardness is >50 N after pressing >100 N after further 24 h.

EXAMPLE 2.1

Paracetamol 50 Mg Effervescent Tablet

| | |
|---|---|
| 25.000 kg | Paracetamol |
| 1.750 kg | sodium saccharinate |
| 15.000 kg | maltodextrine |
| 4.000 kg | fruit flavour | are mixed for 3 min in the high shear mixer 4.

0.150 kg propylglycol are added and the mixture is once again briefly mixed.

The Paracetamol-sweetener-flavour-concentrate is mixed in an air-conditioned room (relative humidity <25%) in the blender 7 with

| | |
|---|---|
| 35.000 kg | citric acid |
| 69.000 kg | sodium bicarbonate | for about 10 to 15 min.

The obtained 149.900 kg tablet blend is pressed by a tablet compressor under external lubrication with less than 0.100 kg magnesium stearate into 50.000 round tablets with a diameter of 22 mm and a tablet weight of 3 g.

EXAMPLE 2.2

Paracetamol+Vitamin C Effervescent Tablet

| | |
|---|---|
| 25.000 kg | Paracetamol |
| 10.000 kg | ascorbic acid |
| 1.750 kg | sodium saccharinate |
| 7.500 kg | maltodextrine |
| 7.500 kg | Karion Instant |
| 4.000 kg | fruit flavour | are mixed for 3 min in the high shear mixer.

0.150 kg propylglycol are added and this mixture is once again briefly mixed.

The Paracetamol-vitamin C-sweetener-flavour-concentrate is mixed in an air-conditioned room (relative humidity <25%) in the blender 7 with

| | |
|---|---|
| 41.000 kg | citric acid |
| 53.250 kg | sodium bicarbonate | for about 10 to 15 min.

The obtained 150.150 kg tablet blend is pressed by a tablet compressor under external lubrication with less than 0.100 kg magnesium stearate into 50.000 round tablets with a diameter of 22 mm and a tablet weight of 3 g.

The tablet hardness is 30 to 50 N.

EXAMPLE 3.1

Acetylcysteine 100 mg Effervescent Tablet

| | |
|---|---|
| 5.000 kg | acetylcysteine |
| 1.000 kg | Aspartam |
| 2.000 kg | fruit flavour | are mixed for 3 min in the high shear mixer.

0.0075 kg propylglycol are added and the mixture is once again briefly mixed.

The acetylcysteine-sweetener-flavour-concentrate is mixed in an air-conditioned room (relative humidity <25%) in the blender 7 with

| | |
|---|---|
| 78.950 kg | citric acid |
| 58.030 kg | sodium bicarbonate | for about 10 to 15 min.

The obtained 144.975 kg tablet blend is pressed by a tablet compressor under external lubrication with less than 0.025 kg magnesium stearate into 50.000 round tablets with a diameter of 22 mm and a tablet weight of 2.9 g.

The tablet hardness is 40 to 50 N.

EXAMPLE 3.2

Acetylcysteine 400 mg Effervescent Tablet

| | |
|---|---|
| 20.000 kg | acetylcysteine |
| 1.000 kg | Aspartam |
| 2.500 kg | fruit flavour | are mixed for 3 min in the high shear mixer.

0.006 kg propylglycol are added and the mixture is once again briefly mixed.

The acetylcysteine-sweetener-flavour-concentrate is mixed in an air-conditioned room (relative humidity <25%) in the blender 7 with

| | |
|---|---|
| 66.650 kg | citric acid |
| 52.841 kg | sodium bicarbonate | for about 10 to 15 min.

The obtained 142.977 kg tablet blend is pressed by a tablet compressor under external lubrication with less than 0.025 kg magnesium stearate into 50.000 round tablets with a diameter of 22 mm and a tablet weight of 2.86 g.

The tablet hardness is 40 to 60 N.

EXAMPLE 4.1

Ambroxol 30 mg Effervescent Tablet

| | |
|---|---|
| 3.000 kg | Ambroxol |
| 0.400 kg | sodium bicarbonate |

-continued

| | |
|---|---|
| 1.125 kg | Aspartam |
| 0.030 kg | Kollidon 25 |
| 0.050 kg | Macrogol 6000 |
| 25.510 kg | maltodextrine |
| 25.510 kg | Karion instant |
| 5.000 kg | fruit flavour | are mixed for 3 min in the high shear mixer.

0.375 kg propylglycol are added and the mixture is once again briefly mixed.

The Ambroxol-colouring-sweetener-flavour-concentrate is mixed in an air-conditioned room (relative humidity <25%) in the blender 7 with

| | |
|---|---|
| 118.850 kg | citric acid |
| 100.150 kg | sodium bicarbonate | for about 10 to 15 min.

The obtained 280.000 kg tablet blend is pressed by a tablet compressor under external lubrication with less than 0.050 kg magnesium stearate into 100.000 round tablets with a diameter of 22 mm and a tablet weight of 2.8 g.

The tablet hardness is >50 N right after preforming.

EXAMPLE 4.2

Ambroxol 60 mg Effervescent Tablet

| | |
|---|---|
| 6.000 kg | Ambroxol |
| 0.500 kg | sodium saccharinate |
| 1.100 kg | Aspartam |
| 0.030 kg | Kollidon 25 |
| 0.050 kg | Macrogol 6000 |
| 23.160 kg | maltodextrine |
| 23.160 kg | Karion instant |
| 6.000 kg | fruit flavour | are mixed for 3 min in the high shear mixer.

0.400 kg propylglycol are added and the mixture is once again briefly mixed.

The Ambroxol-colouring-sweetener-flavour-concentrate is mixed in an air-conditioned room (relative humidity <25%) in the blender 7 with

| | |
|---|---|
| 119.180 kg | citric acid |
| 100.420 kg | sodium bicarbonate | for about 10 to 15 min.

The obtained 280.000 kg tablet blend is pressed by a tablet compressor under external lubrication with less than 0.050 kg magnesium stearate into 100.000 round tablets with a diameter of 22 mm and a tablet weight of 2.8 g.

The tablet hardness is >50 N directly right after pressing.

EXAMPLE 5

Cimetidine 200 mg Effervescent Tablet

| | |
|---|---|
| 10.000 kg | Cimetidine |
| 2.000 kg | sodium cyclamate |
| 0.500 kg | sodium saccharinate |
| 20.000 kg | sorbitol |
| 8.000 kg | fruit flavour | are mixed for 3 min in the high shear mixer.

0.500 kg propylglycol are added and the mixture is once again briefly mixed.

The Cimetidine-colouring-sweetener-flavour-concentrate is mixed in an air-conditioned room (relative humidity <25%) in the blender 7 with

| | |
|---|---|
| 42.500 kg | citric acid |
| 75.500 kg | sodium bicarbonate | for about 10 to 15 min.

The obtained 159.000 kg tablet blend is pressed by a tablet compressor under external lubrication with less than 0.075 kg magnesium stearate into 100.000 round tablets with a diameter of 22 mm and a tablet weight of 3.18 g.

The tablet hardness is 40 to 70 N.

EXAMPLE 6.1

Vitamin C 225 mg Effervescent Tablet

| | |
|---|---|
| 11.250 kg | ascorbic acid |
| 1.000 kg | sodium cyclamate |
| 0.350 kg | sodium saccharinate |
| 0.005 kg | riboflavin |
| 20.000 kg | sorbitol |
| 2.500 kg | maltodextrine |
| 0.500 kg | fruit flavour | are mixed for 3 min in the high shear mixer.

0.125 kg propylglycol are added and the mixture is once again briefly mixed.

The ascorbic acid-colouring-sweetener-flavour-concentrate is mixed in an air-conditioned room (relative humidity <25%) in the blender 7 with

| | |
|---|---|
| 94.145 kg | citric acid |
| 70.000 kg | sodium bicarbonate | for about 10 to 15 min.

The obtained 199.875 kg tablet blend is pressed by a tablet compressor under external lubrication with less than 0.125 kg magnesium stearate into 50.000 round tablets with a diameter of 25 mm and a tablet weight of 4 g.

EXAMPLE 6.2

Vitamin C 500 mg Effervescent Tablet

| | |
|---|---|
| 25.000 kg | ascorbic acid |
| 1.500 kg | sodium cyclamate |
| 0.500 kg | sodium saccharinate |
| 0.075 kg | riboflavin |
| 0.050 kg | beta-carotin |
| 6.000 kg | sorbitol |
| 1.500 kg | fruit flavour | are mixed for 3 min in the high shear mixer.

0.250 kg propylglycol are added and the mixture is once again briefly mixed.

The ascorbic acid-colouring-sweetener-flavour-concentrate is mixed in an air-conditioned room (relative humidity <25%) in the blender 7 with

| | |
|---|---|
| 29.000 kg | citric acid |
| 36.000 kg | sodium bicarbonate | for about 10 to 15 min.

The obtained 99.875 kg tablet blend is pressed by a tablet compressor under external lubrication with less than 0.125 kg silicone oil into 50.000 round tablets with a diameter of 20 mm and a tablet weight of 2 g.

EXAMPLE 6.3

Vitamin C 1000 mg Effervescent Tablet

| | |
|---|---|
| 50.000 kg | ascorbic acid |
| 2.500 kg | sodium cyclamate |
| 0.500 kg | sodium saccharinate |
| 0.750 kg | Kollidon 30 |
| 4.000 kg | maltodextrine |
| 8.500 kg | sorbitol |
| 2.500 kg | fruit flavour | are mixed for 3 min in the high shear mixer.

0.500 kg propylglycol are added and the mixture is once again briefly mixed.

The ascorbic acid-colouring-sweetener-flavour-concentrate is mixed in an air-conditioned room (relative humidity <25%) in the blender 7 with

| | |
|---|---|
| 0.500 kg | citric acid |
| 32.400 kg | mono sodium citrate |
| 29.750 kg | sodium bicarbonate | for about 10 to 15 min.

The obtained 131.900 kg tablet blend is pressed by a tablet compressor under external lubrication with less than 0.100 kg silicone oil into 50.000 round tablets with a diameter of 22 mm and a tablet weight of 2.64 g.

EXAMPLE 7.1

Calcium Gluconate Effervescent Tablet

| | |
|---|---|
| 50.000 kg | calcium gluconate monohydrate |
| 2.000 kg | sodium cyclamate |
| 0.650 kg | sodium saccharinate |
| 0.005 kg | riboflavin |
| 4.000 kg | Karion Instant |
| 1.750 kg | fruit flavour | are mixed for 3 min in the high shear mixer.

0.750 kg propylglycol are added and the mixture is once again briefly mixed.

The calcium-colouring-sweetener-flavour-concentrate is mixed in an air-conditioned room (relative humidity <25%) in the blender 7 with

| | |
|---|---|
| 97.000 kg | citric acid |
| 54.000 kg | sodium bicarbonate | for about 10 to 15 min.

The obtained 210.200 kg tablet blend is pressed by a tablet compressor under external lubrication with less than 0.050 kg magnesium stearate into 50.000 round tablets with a diameter of 25 mm and a tablet weight of 4.2 g.

The tablet hardness is 40 to 50 N.

EXAMPLE 7.2

Calcium 500 mg Effervescent Tablet

| | |
|---|---|
| 150.000 kg | calcium carbonate |
| 4.800 kg | sodium cyclamate |
| 1.440 kg | sodium saccharinate |
| 0.012 kg | riboflavin |
| 3.600 kg | Karion Instant |
| 4.200 kg | fruit flavour | are mixed for 3 min in the high shear mixer.

3.600 kg propylglycol are added and the mixture is once again briefly mixed.

The calcium-colouring-sweetener-flavour-concentrate is mixed in an air-conditioned room (relative humidity <25%) in the blender 7 with

| | |
|---|---|
| 433.788 kg | citric acid |
| 178.560 kg | sodium bicarbonate | for about 10 to 15 min.

The obtained 779.800 kg tablet blend is pressed by a tablet compressor under external lubrication with less than 0.200 kg magnesium stearate into 120.000 round tablets with a diameter of 25 mm and a tablet weight of 6.5 g.

The tablet hardness is 40 to 50 N.

EXAMPLE 7.3

Calcium 500 mg Effervescent Tablet (Without Sodium)

| | |
|---|---|
| 62.500 kg | calcium carbonate |
| 1.000 kg | sodium cyclamate |
| 0.350 kg | sodium saccharinate |
| 2.000 kg | maltodextrine |
| 1.500 kg | fruit flavour | are mixed for 3 min in the high shear mixer.

2.500 kg propylglycol are added and the mixture is once again briefly mixed.

The calcium-colouring-sweetener-flavour-concentrate is mixed in an air-conditioned room (relative humidity <25%) in the blender 7 with

| | |
|---|---|
| 100.000 kg | citric acid | for about 10 to 15 min.

The obtained 169.850 kg tablet blend is pressed by a tablet compressor under external lubrication with less than 0.150 kg silicone oil into 50.000 round tablets with a diameter of 22 mm and a tablet weight of 3.4 g.

EXAMPLE 7.4

Calcium+Vitamin C Effervescent Tablet

| | |
|---|---|
| 150.000 kg | calcium carbonate |
| 15.000 kg | ascorbic acid |
| 5.400 kg | sodium cyclamate |
| 1.440 kg | sodium saccharinate |
| 0.180 kg | riboflavin |
| 2.400 kg | beetroot powder |
| 4.620 kg | fruit flavour | are mixed for 3 min in the high shear mixer.

3.000 kg propylglycol are added and the mixture is once again briefly mixed.

The calcium-vitamin C-colouring-sweetener-flavour-concentrate is mixed in an air-conditioned room (relative humidity <25%) in the blender 7 with

| | |
|---|---|
| 426.360 kg | citric acid |
| 171.600 kg | sodium bicarbonate | for about 10 to 15 min.

The obtained 780.000 kg tablet blend is pressed by a tablet compressor under external lubrication with less than 0.200 kg magnesium stearate into 120.000 round tablets with a diameter of 25 mm and a tablet weight of 6.5 g.

The tablet hardness is 40 to 50 N.

EXAMPLE 8.1

Magnesium 150 mg Effervescent Tablet

| | |
|---|---|
| 140.400 kg | magnesium hydroxide carbonate |
| 9.600 kg | sodium cyclamate |
| 3.000 kg | sodium saccharinate |
| 0.048 kg | riboflavin |
| 12.000 kg | maltodextrine |
| 12.480 kg | fruit flavour | are mixed for 3 min in the high shear mixer.

7.200 kg propylglycol are added and the mixture is once again briefly mixed.

The magnesium-colouring-sweetener-flavour-concentrate is mixed in an air-conditioned room (relative humidity <25%) in the blender 7 with

| | |
|---|---|
| 844.392 kg | citric acid |
| 530.880 kg | sodium bicarbonate | for about 10 to 15 min.

The obtained 1559.800 kg tablet blend is pressed by a tablet compressor under external lubrication with less than 0.200 kg magnesium stearate into 240.000 round tablets with a diameter of 25 mm and a tablet weight of 6.5 g.

The tablet hardness is 50 to 70 N.

EXAMPLE 8.2

Magnesium+Vitamin C Effervescent Tablet

| | |
|---|---|
| 81.960 kg | magnesium carbonate |
| 15.000 kg | ascorbic acid |
| 4.200 kg | sodium cyclamate |
| 1.200 kg | sodium saccharinate |
| 12.000 kg | maltodextrine |
| 4.800 kg | fruit flavour | are mixed for 3 min in the high shear mixer.

3.600 kg propylglycol are added and the mixture is once again briefly mixed.

The magnesium-vitamin C-colouring-sweetener-flavour-concentrate is mixed in an air-conditioned room (relative humidity <25%) in the blender 7 with

| | |
|---|---|
| 2.160 kg | beetroot powder |
| 0.720 kg | riboflavin |
| 427.550 kg | citric acid |
| 226.800 kg | sodium bicarbonate | for about 10 to 15 min.

The obtained 779.800 kg tablet blend is pressed by a tablet compressor under external lubrication with less than 0.200 kg magnesium stearate into 120.000 round tablets with a diameter of 25 mm and a tablet weight of 6.5 g.

The tablet hardness is 50 to 70 N.

EXAMPLE 9

Vitamin E Effervescent Tablet

| | |
|---|---|
| 7.500 kg | vitamin E acetate |
| 1.250 kg | sodium saccharinate |
| 28.000 kg | maltodextrine |
| 1.250 kg | beetroot powder |
| 0.250 kg | riboflavin |
| 2.000 kg | Karion Instant |
| 1.250 kg | fruit flavour | are mixed for 3 min in the high shear mixer.

0.125 kg propylglycol are added and the mixture is once again briefly mixed.

The vitamin E-colouring-sweetener-flavour-concentrate is mixed in an air-conditioned room (relative humidity <25%) in the blender 7 with

| | |
|---|---|
| 97.250 kg | citric acid |
| 66.000 kg | sodium bicarbonate | for about 10 to 15 min.

The obtained 204.875 kg tablet blend is pressed by a tablet compressor under external lubrication with less than 0.125 kg silicone oil into 50.000 round tablets with a diameter of 25 mm and a tablet weight of 4.1 g.

EXAMPLE 10.1

Multi-vitamin Effervescent Tablet

| | |
|---|---|
| 72.000 kg | multi-vitamin mixture |
| 6.300 kg | sodium cyclamate |
| 4.980 kg | sodium saccharinate |
| 40.500 kg | Karion Instant |
| 24.300 kg | maltodextrine |
| 4.500 kg | fruit flavour | are mixed for 3 min in the high shear mixer.

1.260 kg propylglycol are added and the mixture is once again briefly mixed.

The multi-vitamin-colouring-sweetener-flavour-concentrate is mixed in an air-conditioned room (relative humidity <25%) in the blender 7 with

| | |
|---|---|
| 2.700 kg | beetroot powder |
| 404.460 kg | citric acid |
| 252.000 kg | sodium bicarbonate | for about 10 to 15 min.

The obtained 809.500 kg tablet blend is pressed by a tablet compressor under external lubrication with less than 0.500 kg magnesium stearate into 180.000 round tablets with a diameter of 25 mm and a tablet weight of 4.5 g.

The tablet hardness is 70 to 80 N.

EXAMPLE 10.2

Multi-vitamin+Minerals Effervescent Tablet

| | |
|---|---|
| 72.000 kg | multi-vitamin mixture |
| 45.000 kg | calcium carbonate |
| 79.200 kg | potassium hydrogen phosphate |
| 21.870 kg | magnesium carbonate |
| 6.300 kg | sodium saccharinate |
| 18.900 kg | maltodextrine |
| 9.000 kg | fruit flavour | are mixed for 3 min in the high shear mixer.

4.500 kg propylglycol are added and the mixture is once again briefly mixed.

The multi-vitamin-mineral-colouring-sweetener-flavour-concentrate is mixed in an air-conditioned room (relative humidity <25%) in the blender 7 with

| | |
|---|---|
| 3.600 kg | beetroot powder |
| 400.500 kg | citric acid |
| 108.000 kg | sodium bicarbonate |
| 24.300 kg | sodium carbonate |
| 16.830 kg | potassium bicarbonate | for about 10 to 15 min.

The obtained 809.500 kg tablet blend is pressed by a tablet compressor under external lubrication with less than 0.500 kg magnesium stearate into 180.000 round tablets with a diameter of 25 mm and a tablet weight of 4.5 g.

The tablet hardness is 80 to 90 N.

EXAMPLE 11

Carotin+Vitamin C+E Effervescent Tablet

| | |
|---|---|
| 14.000 kg | Protector Mixture |
| 3.750 kg | ascorbic acid |
| 0.500 kg | calcium pantothenate |
| 31.250 kg | calcium carbonate |
| 8.750 kg | magnesium carbonate |
| 0.0001 kg | Biotin |
| 1.500 kg | natrium cyclamate |
| 0.750 kg | natrium saccharinate |
| 2.500 kg | fruit flavour | are mixed for 3 min in the high shear mixer.

1.000 kg propylglycol are added and the mixture is once again briefly mixed.

The carotin-vitamin E+C-colouring-sweetener-flavour-concentrate is mixed in an air-conditioned room (relative humidity <25%) in the blender 7 with

| | |
|---|---|
| 126.000 kg | citric acid |
| 30.000 kg | sodium bicarbonate | for about 10 to 15 min.

The obtained 219.875 kg tablet blend is pressed by a tablet compressor under external lubrication with less than 0.125 kg silicone oil into 50.000 round tablets with a diameter of 25 mm and a tablet weight of 4.4 g. 280 mg Protector Mixture which are provided per effervescent tablet contain 6 mg beta-carotin, 12 mg vitamin E and 75 mg vitamin C.

EXAMPLE 12

Iron+Vitamin C Effervescent Tablet

| | |
|---|---|
| 38.850 kg | iron-II-gluconate hydrate |
| 31.250 kg | ascorbic acid |
| 0.0015 kg | vitamin B 12 |
| 0.050 kg | folic acid |
| 7.500 kg | sodium cyclamate |
| 4.500 kg | sodium saccharinate |
| 125.000 kg | maltodextrine |
| 15.000 kg | Karion Instant |
| 5.000 kg | fruit flavour | are mixed for 3 min in the high shear mixer.

1.250 kg propylglycol are added and the mixture is once again briefly mixed.

The iron-vitamin C-colouring-sweetener-flavour-concentrate is mixed in an air-conditioned room (relative humidity <25%) in the blender 7 with

| | |
|---|---|
| 0.250 kg | riboflavin |
| 11.250 kg | beetroot powder |
| 810.100 kg | citric acid |
| 575.000 kg | sodium bicarbonate | for about 10 to 15 min.

The obtained 1624.502 kg tablet blend is pressed by a tablet compressor under external lubrication with less than 0.500 kg magnesium stearate into 250.000 round tablets with a diameter of 25 mm and a tablet weight of 6.5 g.

The tablet hardness is 45 to 60 N.

The following table 1 shows the dissolving time of the effervescent tablets of the examples 1 to 12. There, one can also see the amount of the sherbets and the amount of the binder each per weight of whole effervescent tablets.

The dissolving time is the time in which the effervescent tablets brought into water are dissolved and the gas production is completed without any particles remaining. The measuring of the dissolving time in seconds happens with each tablet being brought in 150 ml water at a temperature of 20° C. Therein, the dissolving time is determined by the mean.

Table 1 shows that effervescent tablets produced according to the method of the invention have a considerable shorter dissolving time compared to the dissolving time of 300 sec. according to the European Book of Pharmacy, 2nd edition.

It can also be seen that the amount of sherbets, which can be reliably introduced with the new binders into mechanically stable effervescent tablets, is very high. This is also a reason for the fast dissolving of the effervescent tablets besides the characteristics of the binder itself. If the amount of sherbets is noted as a range, this means that the active substance or parts of the combination of substances also function as sherbets.

On the other hand, the part of the active substance or of the combination of active substances, of the carriers, and of the binder which is the part of the tablet blend that is to be mixed in the high shear mixer is relatively small as compared to the whole weight of the effervescent tablets in comparison with the conditions known from literature. This means that the active substance or the combination of active substances can be more easily measured into exact doses.

The amount of binder in the new effervescent tablets is extremely small.

TABLE 1

| | Effervescent tablets | | |
|---|---|---|---|
| Example | dissolving time [sec] | amount of sherbets [%] | amount of binder [%] |
| 1.1 | <60 | 78.89 | 0.0185 |
| 1.2 | <120 | 80.97 | 0.0139 |
| 2.1 | 150 | 69.33 | 0.1000 |
| 2.2 | <120 | 62.73 | 0.0998 |
| 3.1 | <60 | 94.47 | 0.0052 |
| 3.2 | <120 | 83.56 | 0.0042 |
| 4.1 | <70 | 78.21 | 0.1339 |
| 4.2 | <70 | 78.43 | 0.1429 |
| 5 | <100 | 74.21 | 0.3145 |
| 6.1 | 120 | 82.07 | 0.0625 |
| 6.2 | 180 | 65.00 | 0.2500 |
| 6.3 | 150 | 47.46–8.3 | 0.3788 |
| 7.1 | 100 | 71.90 | 0.3567 |
| 7.2 | 100 | 78.51 | 0.4615 |
| 7.3 | 180 | 58.82–9.5 | 1.4706 |
| 7.4 | 60 | 76.66 | 0.3846 |
| 8.1 | 100 | 88.16 | 0.4615 |
| 8.2 | 120 | 83.89 | 0.4615 |
| 9 | 90 | 79.63 | 0.0610 |
| 10.1 | 60 | 81.04 | 0.1556 |
| 10.2 | 90 | 67.86 | 0.5556 |
| 11 | 100 | 70.91 | 0.4545 |
| 12 | 45 | 85.23 | 0.0769 |

What I claim is:

1. A method of producing effervescent tablets, the tablets comprising at least one active substance and sherbets, said method comprising the steps of:
   providing at least one active substance,
   providing at least one binder, wherein the binder is a material selected from the group consisting of propylglycol and glycerin,
   mixing the active substances with the binder in an atmosphere having a relative humidity of at least approximately 25% to form a first mixture,
   adding sherbet to the first mixture in an atmosphere having a relative humidity of less than approximately 25% such that a second mixture is formed, the sherbet comprising a base component and an acid component, wherein the base component is a material selected from the group consisting of sodium carbonate, sodium hydrogen carbonate, potassium carbonate, potassium hydrogen carbonate, and calcium carbonate, and wherein the acid component is a material selected from the group consisting of ascorbic acid mono sodium citrate, wine acid and citric acid, and
   forming the second mixture into tablets.

2. A method of producing effervescent tablets, the tablets comprising at least one active substance, at least one carrier, and at least one sherbet, wherein the carrier is a material selected from the group consisting of sweeteners, flavours, colourings, scents, softeners, and bleaches, said method comprising the steps of:
   providing at least one active substance,
   providing at least one carrier,
   providing at least one binder, wherein the binder is a material selected from the group consisting of propylglycol and glycerin, mixing the active substances and carriers with the binder in an atmosphere having a relative humidity of at least approximately 25% to form a first mixture, adding sherbet to the first mixture in an atmosphere having a relative humidity of less than approximately 25% such that a second mixture is formed, the sherbet comprising a base component and an acid component, and forming the second mixture into tablets.

3. A method of producing effervescent tablets, comprising the steps of:

providing at least one active substance, providing at least one binder, wherein the binder is a material selected from the group consisting of propylglycol and glycerin, mixing the active substances with the binder in an atmosphere having a relative humidity of at least approximately 25% to form a first mixture, adding sherbet to the first mixture in an atmosphere having a relative humidity of less than approximately 25% such that a second mixture is formed, the sherbet comprising a base component and an acid component, and forming the second mixture into tablets.

4. A method according to claim 1, wherein the step of mixing comprises mixing the active substances and binder in a shear mixer for at least approximately 3 minutes.

5. A method according to claim 1, wherein the second mixture is directly formed into tablets.

6. A method according to claim 1, wherein the binder is used in an amount of 0.004 to 2.5% per weight of the whole effervescent tablet.

7. A method according to claim 6, wherein the binder is used in an amount of 0.004 to 1.5% per weight of the whole effervescent tablet.

8. A method according to claim 7, wherein the binder is used in an amount of 0.01 to 1.0% per weight of the whole effervescent tablet.

9. A method according to claim 1, wherein the sherbets are used in an amount of 58 to 93% per weight of the whole effervescent tablet.

10. A method according to claim 9, wherein the sherbets are used in an amount of 70 to 90% per weight of the whole effervescent tablet.

11. A method according to claim 3, wherein the sherbet is used in an amount of 58 to 93% per weight of the whole effervescent tablet.

12. A method according to claim 3, wherein the sherbet is used in an amount of 70 to 90% per weight of the whole effervescent tablet.

13. A method according to claim 2, wherein the step of mixing the active substances and carriers comprises mixing the active substances and carriers in a mixer for at least approximately 3 minutes prior to adding the sherbet.

14. A method according to claim 2, wherein the sherbet is used in an amount of 58 to 93% per weight of the whole effervescent tablet.

15. A method according to claim 2, wherein the sherbet is used in an amount of 70 to 90% per weight of the whole effervescent tablet.

* * * * *